(12) United States Patent
Leyva et al.

(10) Patent No.: US 7,247,025 B1
(45) Date of Patent: *Jul. 24, 2007

(54) SEQUENTIAL REASONING TESTING SYSTEM AND METHOD

(75) Inventors: Laura Leyva, San Antonio, TX (US); David Tulsky, Summit, NJ (US)

(73) Assignee: Harcourt Assessment, Inc., San Antonio, TX (US)

( * ) Notice: Subject to any disclaimer, the term of this patent is extended or adjusted under 35 U.S.C. 154(b) by 456 days.

This patent is subject to a terminal disclaimer.

(21) Appl. No.: 10/737,192

(22) Filed: Dec. 16, 2003
(Under 37 CFR 1.47)

Related U.S. Application Data

(63) Continuation of application No. 10/123,037, filed on Apr. 15, 2002, now Pat. No. 6,663,392.

(60) Provisional application No. 60/285,950, filed on Apr. 24, 2001.

(51) Int. Cl.
*G09B 19/00* (2006.01)

(52) U.S. Cl. .................. 434/236; 434/237; 434/238

(58) Field of Classification Search .......... 434/236, 434/238
See application file for complete search history.

(56) References Cited

U.S. PATENT DOCUMENTS

| | | | |
|---|---|---|---|
| 1,139,256 A | 5/1915 | Clark | |
| 2,359,460 A | 10/1944 | Barens | |
| 3,543,418 A | 12/1970 | Press | |
| 3,755,921 A | 9/1973 | Heller | |
| 4,207,087 A | 6/1980 | Morrison et al. | |
| 4,770,636 A | 9/1988 | Buschke | |
| 5,017,142 A | 5/1991 | Bemis et al. | |
| 5,079,726 A | 1/1992 | Keller | |
| 5,295,491 A * | 3/1994 | Gevins ................. | 600/544 |
| 5,411,271 A | 5/1995 | Mirando | |
| 5,533,902 A | 7/1996 | Miller | |
| 5,885,083 A * | 3/1999 | Ferrell ................. | 434/156 |
| 5,911,581 A | 6/1999 | Reynolds et al. | |
| 6,030,226 A | 2/2000 | Hersh | |
| 6,053,739 A | 4/2000 | Stewart et al. | |
| 6,097,981 A * | 8/2000 | Freer ................... | 600/545 |
| 6,159,014 A | 12/2000 | Jenkins et al. | |
| 6,231,344 B1 * | 5/2001 | Merzenich et al. ... | 434/236 |
| 6,306,086 B1 | 10/2001 | Buschke | |
| 6,346,043 B1 * | 2/2002 | Colin et al. .......... | 463/17 |
| 6,663,392 B2 * | 12/2003 | Leyva et al. ......... | 434/236 |

* cited by examiner

*Primary Examiner*—Robert E. Pezzuto
*Assistant Examiner*—Binh-An D. Nguyen
(74) *Attorney, Agent, or Firm*—Allen, Dyer, Doppelt, Milbrath & Gilchrist, P.A.

(57) ABSTRACT

A method for testing a working memory and fluid reasoning of a subject includes the step of sequentially presenting to a subject a first plurality of images, wherein each image is positioned in a different sector of a display device. The first plurality of images totals one fewer than a total number of sectors. Next the subject is simultaneously presented with a second plurality of images. One of the second plurality of images bears an analogous relationship to the first plurality of images. The subject is then asked to select an analogous image from the second plurality of images.

12 Claims, 6 Drawing Sheets

SEQUENTIAL REASONING TESTING SYSTEM AND METHOD

CROSS-REFERENCE TO RELATED APPLICATION

This application is a continuation of and incorporates by reference application Ser. No. 10/123,037, filed Apr. 15, 2002, now U.S. Pat. No. 6,663,392, which application claims priority to provisional application 60/285,950, "Sequential Reasoning Testing System and Method," filed Apr. 24, 2001, both of which are commonly owned with the present invention and which are incorporated herein by reference.

BACKGROUND OF THE INVENTION

1. Field of the Invention

The present invention relates to systems and methods for testing intelligence, and, more particularly, to such system and methods for testing working memory and/or fluid reasoning.

2. Description of Related Art

Tests are known in the art for testing a subject's ability to fill in a pattern of images, including those that present a series of images to the subject for subsequent filling in one of a plurality of other images (Clark, U.S. Pat. No. 1,139,256), complete a pattern (Press, U.S. Pat. No. 3,543,418), or perform a matching task (Miller, U.S. Pat. No. 5,533,902; Reynolds et al., U.S. Pat. No. 5,911,581; Hersh, U.S. Pat. No. 6,030,226).

However, there are no tests known in the art that also require an additional memory dimension imposed by removing presented images sequentially.

SUMMARY OF THE INVENTION

It is therefore an object of the present invention to provide a system and method for testing a subject's working memory.

It is a further object to provide such a system and method for testing fluid reasoning.

It is another object to provide such a system and method for testing a combination of working memory and fluid reasoning.

It is also an object to provide such a system and method that provide for adaptive administration.

It is an additional object to provide a method for administering such a test.

It is yet a further object to provide a series of representations for use in such a test.

These and other objects are achieved by the present invention, a method for testing a working memory and fluid reasoning of a subject. The method comprises the step of sequentially presenting to a subject a first plurality of images. Each image is positioned in a different sector of a display device. The first plurality of images totals one fewer than a total number of sectors.

Next the subject is simultaneously presented with a second plurality of images. One of the second plurality of images bears an analogous relationship to the first plurality of images.

The subject is then asked to select an analogous image from the second plurality of images.

The features that characterize the invention, both as to organization and method of operation, together with further objects and advantages thereof, will be better understood from the following description used in conjunction with the accompanying drawing. It is to be expressly understood that the drawing is for the purpose of illustration and description and is not intended as a definition of the limits of the invention. These and other objects attained, and advantages offered, by the present invention will become more fully apparent as the description that now follows is read in conjunction with the accompanying drawing.

DETAILED DESCRIPTION OF THE PREFERRED EMBODIMENTS

Figure 1A:
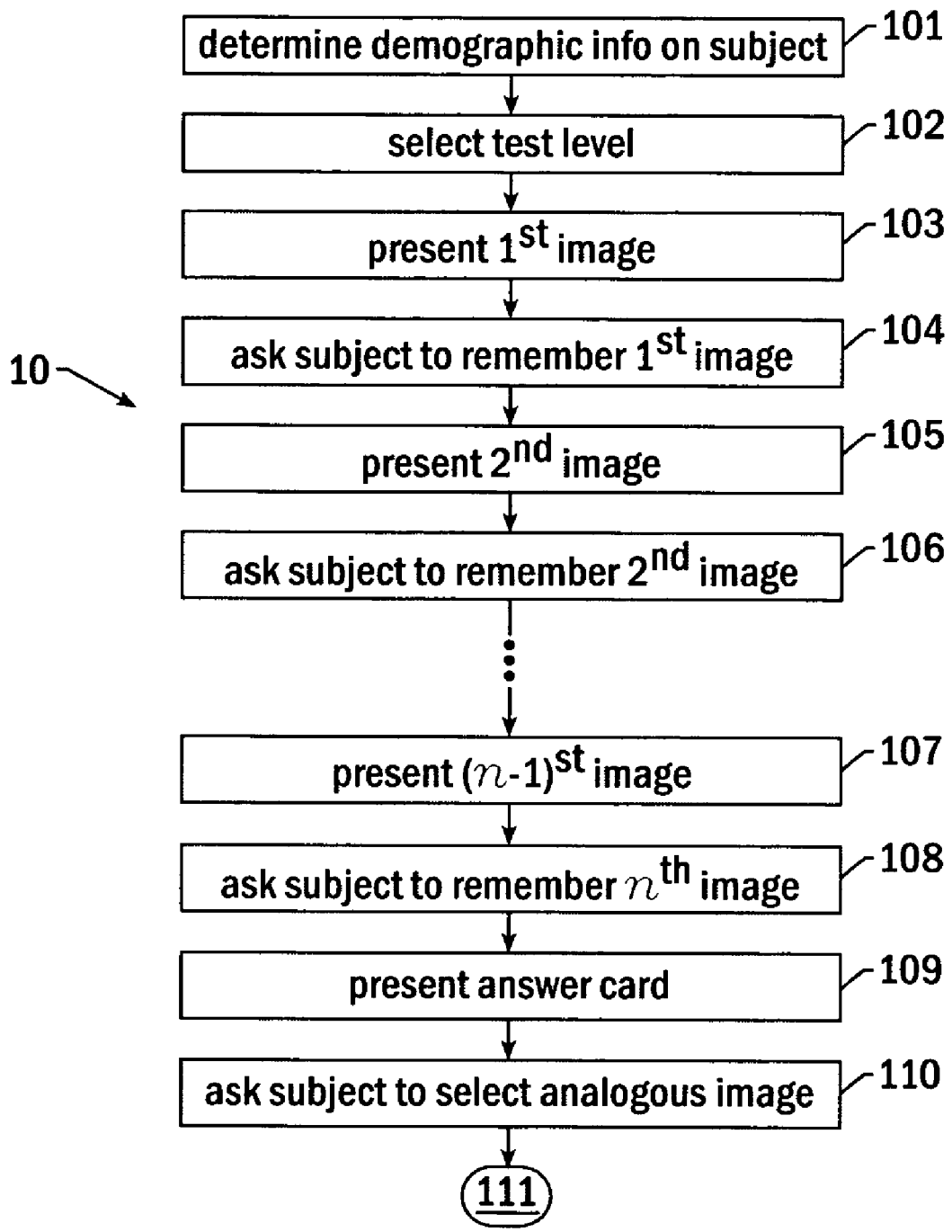
FIGS. 1A,1B is a flowchart outlining an administration of the test of the present invention.
Figure 1B:
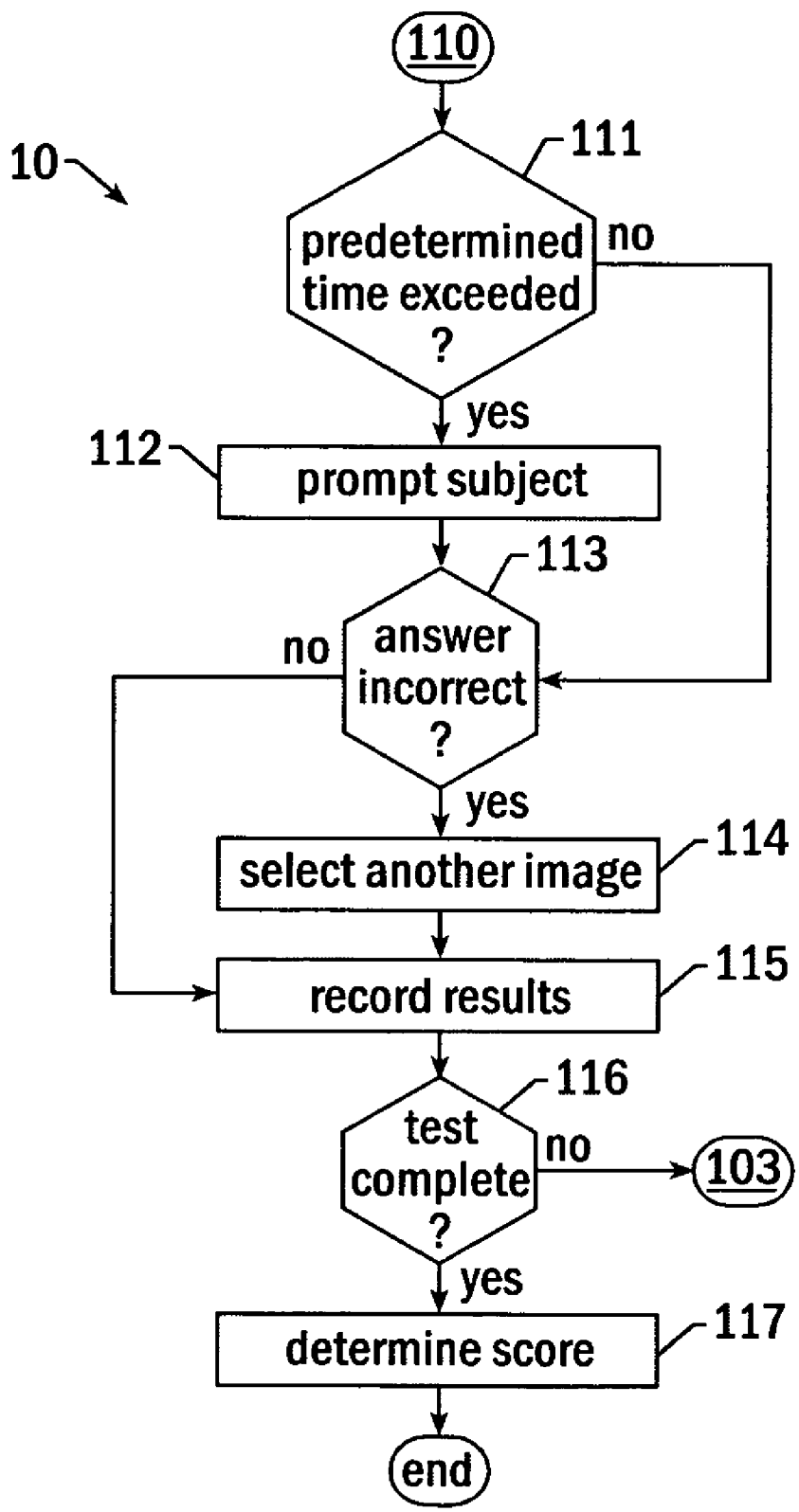

A description of the preferred embodiments of the present invention will now be presented with reference to FIGS. 1A-3B.

An exemplary flowchart of the test administration method (FIGS. 1A, 1B) outlines steps to be taken in giving the working memory and fluid reasoning test 10 for presentation to a subject 20. The method comprises the steps of determining demographic information on the subject 20 (block 101) for the purpose of choosing an appropriate test level (block 102) to be presented. Such demographic information typically includes, but is not intended to be limited to, the subject's age and/or grade level.

Next the subject 20 is presented with a first representation of one of a first plurality of images (block 103). In a first embodiment, this first representation comprises a card or sheet of paper with a matrix of sectors, here four 31-34, thereon, with one of the sectors having a first image therein. An exemplary first representation 30 is given in FIG. 2A, wherein an image 35 of four dots is shown as being positioned within a first sector 31. Sectors 32-34 are blank. Next the subject 20 is asked to look at the first image 35 and remember it (block 104).

The subject 20 is then presented with a second representation 40 of a second of the first plurality of items (FIG. 2B, block 105), with a second image 36 of a square in the second sector 32. Sectors 31,33,34 are blank. The subject 20 is then asked to look at the second image 36 and remember it (block 106).

This process is repeated n–1 times (blocks 107-108), where n is the number of sectors on the matrix. Here, n=4, and thus the third presentation 50 is the final one, with a pentagonal FIG. 37 shown in sector 33 (FIG. 2C), and sectors 31,32,34 are blank. It is obvious to one of skill in the art that n may equal any reasonable number, with n typically an even integer; 4 and 6 are typical numbers.

When all representations 30,40,50 have been viewed, the subject 20 is presented with an nth, here a fourth, representation 60 (FIG. 2D) on an "answer card" 66 (block 109) and is asked to select an analogous image from a second plurality of images 61-65 (block 110). The second plurality of images may comprise a reasonable number from which to choose, typically 4 or 5, although this is not intended as a limitation.

In the test comprising representations as shown in FIGS. 2A-2D, the correct choice would be image 61. If a predetermined time 19 is exceeded by the subject 20 in making a selection (block 111), prompting is given by the test giver 21 (block 112). If an incorrect answer is given (block 113), the subject 20 is asked to select another image from the second plurality of images (block 114). The results are recorded (block 115). Once the test 10 has been completed (block 116), it is scored (block 117), the score indicative of a working memory and fluid reasoning ability of the subject 20.

Figure 2A:
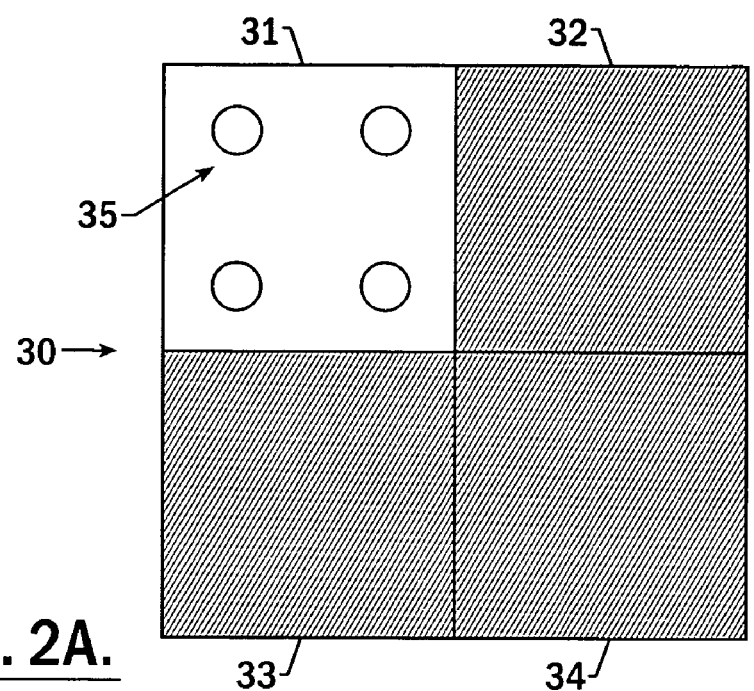
FIGS. 2A-2D is an exemplary series of image cards, including three image cards (FIGS. 2A-2C) and an answer selection card (FIG. 2E).
Figure 2B:
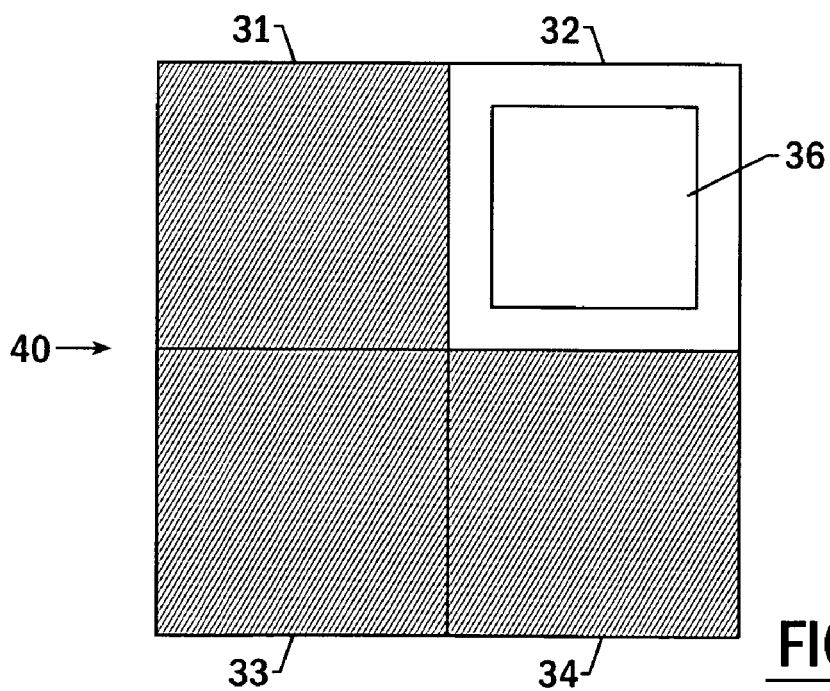
Figure 2C:
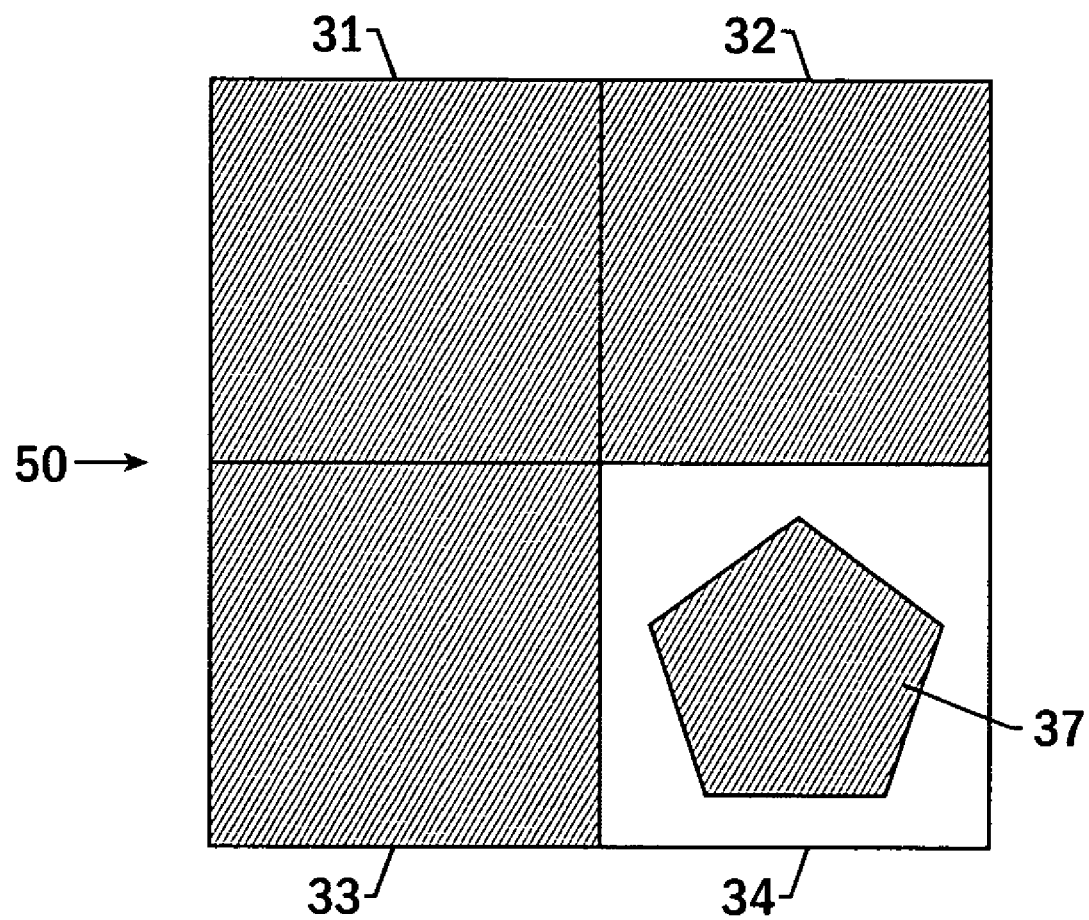
Figure 2D:
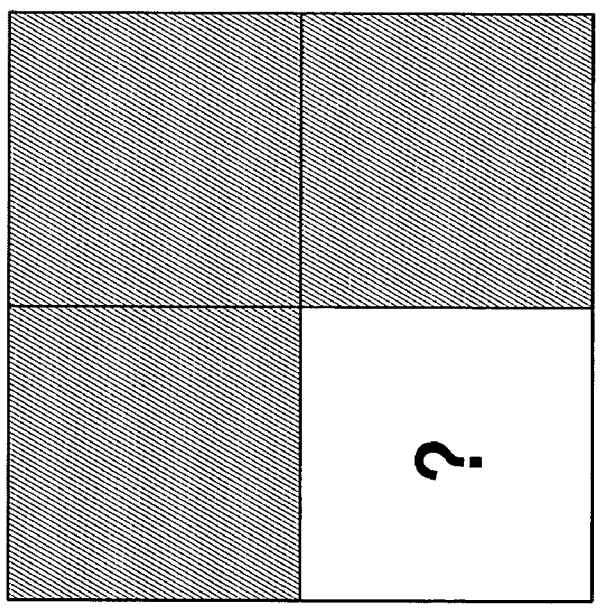
Figure 2D:
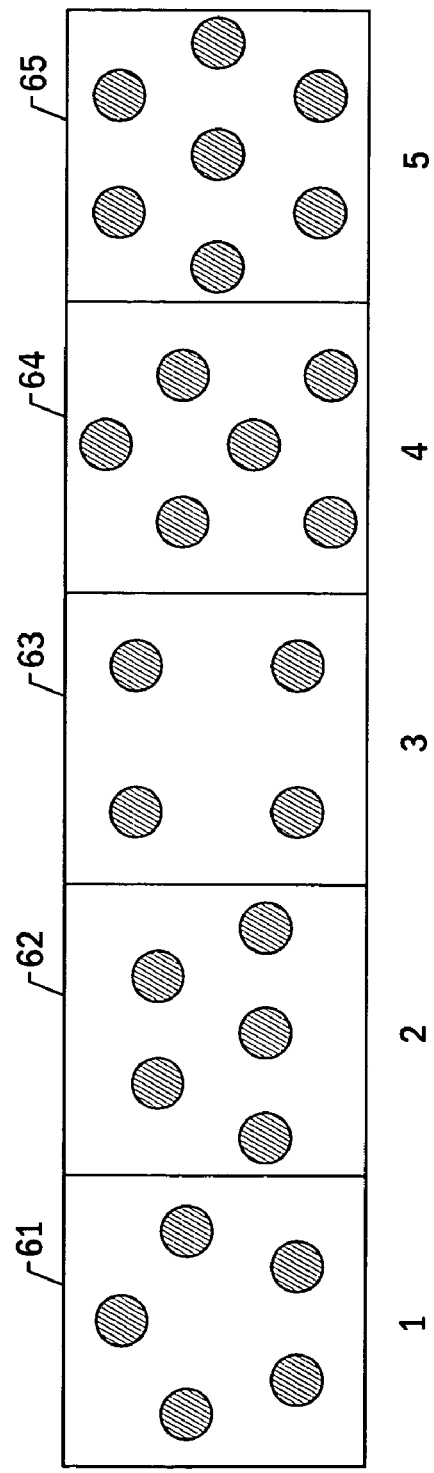

One of skill in the art will recognize that a "manual" or "automated" test administration mode may be contemplated. In a manual mode (FIG. 3A), picture cards 30,40,50 such as those illustrated in FIGS. 2A-2C and an answer representation card 60 such as that illustrated in FIG. 2D are shown to the subject 20 by a human test giver 21, who also manually records the times 19 and responses on a form 29. Scoring may be done either by the test giver 21 or by another entity, such as a testing corporation or computer.

In an automated embodiment (FIG. 3B), the "test giver" comprises a computer 22 having resident thereon a software package 23 adapted to give the test in substantially the same steps as listed above. In communication with and under direction from the computer 22 is a display screen 24, on which may be presented the representations and which, using a keyboard 31 or a pointing device such as a mouse 25 in communication with the computer 22, the subject 20 may make selections. Other forms of receiving communication from the subject 20 may comprise such devices known in the art as a touch screen or a microphone for voice recognition and translation, and the invention is not intended to be limited to particular input/output devices.

The computer 22 further comprises a clock 26 accessible by the software 23 for performing the timing functions. In this automated case, the prompting and asking steps can be performed by displaying a statement or query on the screen 24, or via a speaker 27 in communication with the computer 22, under direction of the software 23.

Scoring in this case could be performed by the software 23 resident in the computer 20. Alternatively, the digital "scoring form," a data record, may be transmitted via modem 28 to a scoring center 80 remote from the test site 11.

Figure 3A:
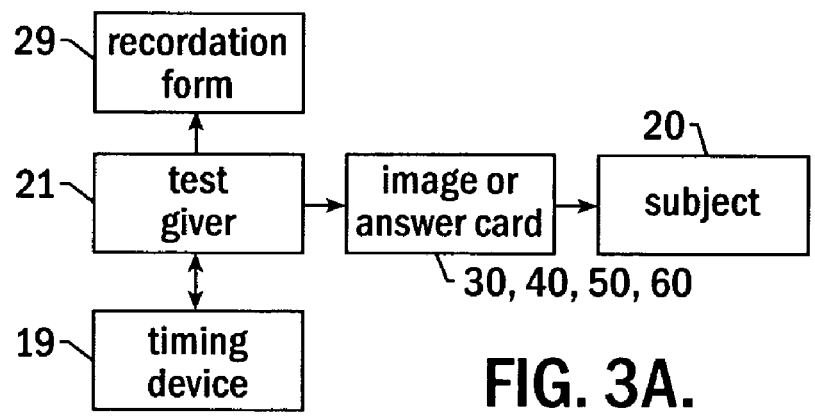
FIGS. 3A,3B are schematic diagrams of a manual (FIG. 3A) and an automated (FIG. 3B) system for administering a test.
Figure 3B:
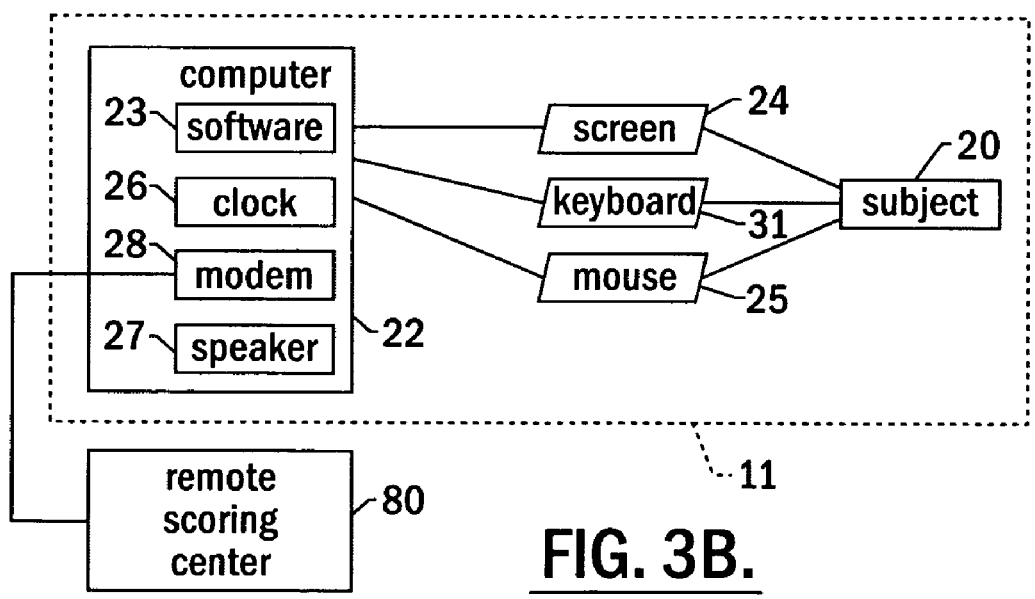

Another benefit of the automated embodiment of FIG. 3B is an ability to perform an adaptive administration of a test. In this case a contemporaneous evaluation of the subject 20 occurs during the test administration, and the software 23 adjusts the presentation of subsequent images based upon the results of previous portions of the test.

It may be appreciated by one skilled in the art that additional embodiments may be contemplated, including alternate representations of items and alternate modes of presenting the items to a subject.

In the foregoing description, certain terms have been used for brevity, clarity, and understanding, but no unnecessary limitations are to be implied therefrom beyond the requirements of the prior art, because such words are used for description purposes herein and are intended to be broadly construed. Moreover, the embodiments of the apparatus illustrated and described herein are by way of example, and the scope of the invention is not limited to the exact details of construction.

Having now described the invention, the construction, the operation and use of preferred embodiment thereof, and the advantageous new and useful results obtained thereby, the new and useful constructions, and reasonable mechanical equivalents thereof obvious to those skilled in the art, are set forth in the appended claims.

What is claimed is:

1. A computer-readable medium having encoded thereon a software program for testing a working memory, the software program comprising:

(a) a code segment for sequentially presenting to a subject a first plurality of images, each image positioned in a different sector of a display device, the first plurality of images totaling one fewer than a total number of sectors;

(b) a code segment for simultaneously presenting to the subject a second plurality of images, one of the second plurality of images bearing an analogous relationship to the first plurality of images;

(c) a code segment for prompting the subject to select an analogous image from the second plurality of images;

a code segment for receiving a response from the subject via an input device; and a code segment for scoring the received responses to determine a working memory and fluid reasoning indicator.

2. The computer-readable medium recited in claim 1, wherein the software program further comprises a code segment adapted to access a clock in a processor and to time an interval between the second plurality of images presentation and a time at which the response is received.

3. The computer-readable medium recited in claim 2, wherein the software program further comprises a code segment for prompting the subject if a predetermined time has been exceeded without receiving a response.

4. The computer-readable medium recited in claim 1, wherein the software program further comprises code segments for:

comparing the received response with a predetermined correct answer;

if the received response is incorrect, outputting to the subject an indication that the response was incorrect; and prompting the subject to select another image from the second plurality of images.

5. The computer-readable medium recited in claim 4, wherein the software program further comprises a code segment for iterating code segments (a)-(c) a predetermined number of times using a first plurality of images selected from a first set thereof and a respective second plurality of images selected from a second set thereof.

6. The computer-readable medium recited in claim 5, wherein the software program further comprises a code segment for, following a predetermined number of iterations, selecting a first and a second set of images from the first and the second set thereof based upon at least one of the received responses.

7. The computer-readable medium recited in claim 1, wherein the software program further comprises a code segment for transmitting the received responses to a remote processor housing the scoring code segment.

8. The program computer-readable medium recited in claim 1, wherein the first plurality of images comprises three or five images, and wherein the second plurality of images comprises four or five images.

9. The computer-readable medium recited in claim 1, wherein the first plurality of images presenting code segment comprises a code segment for sequentially presenting the first plurality of images at predetermined intervals.

10. The computer-readable medium recited in claim 1, wherein the display device comprises a substantially planar matrix comprising the sectors.

11. The computer-readable medium recited in claim 10, wherein the display device comprises a display screen adapted to display a matrix.

12. The computer-readable medium recited in claim 1, wherein the software program further comprises a code segment for requesting the subject to input a demographic indicator of the subject and a code segment for selecting a first and a second plurality of images commensurate with the demographic indicator.

* * * * *